(12) United States Patent
Feeney et al.

(10) Patent No.: US 11,420,024 B2
(45) Date of Patent: Aug. 23, 2022

(54) DRAINAGE TUBING MANAGEMENT DEVICE

(71) Applicant: Medline Industries, LP, Northfield, IL (US)

(72) Inventors: Connor Feeney, Evanston, IL (US); Andrew J. Mills, Highland Park, IL (US)

(73) Assignee: Medline Industries, LP, Northfield, IL (US)

( * ) Notice: Subject to any disclaimer, the term of this patent is extended or adjusted under 35 U.S.C. 154(b) by 192 days.

(21) Appl. No.: 16/775,495

(22) Filed: Jan. 29, 2020

(65) Prior Publication Data
US 2021/0228839 A1 Jul. 29, 2021

(51) Int. Cl.
*A61M 25/02* (2006.01)
*A61M 25/00* (2006.01)

(52) U.S. Cl.
CPC .......... *A61M 25/02* (2013.01); *A61M 25/002* (2013.01); *A61M 25/0017* (2013.01); *A61M 2025/028* (2013.01); *A61M 2209/082* (2013.01)

(58) Field of Classification Search
CPC ............ A61M 39/08; A61M 2209/082; A61M 2025/029; A61M 5/1418; A61M 25/002; A61M 2209/08; A61M 25/02; A61G 7/0503; A61G 2203/78; A47B 23/00; A47B 23/02; A47B 23/025
See application file for complete search history.

(56) References Cited

U.S. PATENT DOCUMENTS

| 4,122,851 A | 10/1978 | Grossner |
| 4,328,917 A | 5/1982 | Reeberg |

(Continued)

FOREIGN PATENT DOCUMENTS

| JP | 2007275599 | 10/2007 |
| WO | 2007092922 | 8/2007 |
| WO | 2015057999 | 4/2015 |

OTHER PUBLICATIONS

International Search Report and Written Opinion for International Application No. PCT/US2021/014140 dated May 12, 2021.

*Primary Examiner* — Adam Marcetich
*Assistant Examiner* — Meagan Ngo
(74) *Attorney, Agent, or Firm* — Fitch, Even, Tabin & Flannery LLP (57) ABSTRACT

A drainage tubing management device is provided. The drainage tubing management device generally comprises a body including a planar field, and having plural pairs of spaced-apart protrusions extending from said field, each pair of protrusions sized to accept flexible drainage tubing therebetween, wherein pairs of the protrusions are arranged in at least first and second rows such that drainage tubing may be retained with respect to said body along the first and second rows, at least one aperture in said body, and a securement mechanism comprising one or more of (a) a post having a longitudinal axis, said post being insertable through within said aperture and having a terminal flange occluding passage of said post through said aperture, said post being sufficiently rigid to support said body and (b) a flexible hanging strap insertable through said aperture and having a terminal flange occluding passage of said strap through said aperture.

9 Claims, 11 Drawing Sheets

(56) References Cited

U.S. PATENT DOCUMENTS

| | | | |
|---|---|---|---|
| 5,271,745 A | | 12/1993 | Fentress |
| 8,807,376 B1 * | | 8/2014 | Mastors ................. A61M 5/14 |
| | | | 220/481 |
| 9,895,486 B1 * | | 2/2018 | Carey-Hench .... A61M 16/0683 |
| 2006/0186010 A1 | | 8/2006 | Warnack |
| 2006/0271019 A1 | | 11/2006 | Stoller |
| 2007/0149914 A1 | | 6/2007 | Axelsson |
| 2007/0282272 A1 | | 12/2007 | Bannon |
| 2008/0097333 A1 | | 4/2008 | Henning |
| 2009/0281502 A1 * | | 11/2009 | Heitkamp ............. A61M 25/02 |
| | | | 604/179 |
| 2010/0094173 A1 | | 4/2010 | Denton |
| 2010/0204573 A1 | | 8/2010 | Spohn |
| 2010/0294821 A1 | | 11/2010 | Szabo |
| 2011/0264061 A1 * | | 10/2011 | Solomon ............. A61G 7/0503 |
| | | | 604/318 |
| 2014/0194839 A1 | | 7/2014 | Torres-Leon |
| 2015/0068941 A1 | | 3/2015 | Caron |
| 2015/0101616 A1 * | | 4/2015 | Wiley .................... A61B 50/20 |
| | | | 128/852 |
| 2015/0144746 A1 * | | 5/2015 | Stewart ............... A61M 5/1418 |
| | | | 248/67.5 |
| 2016/0114103 A1 * | | 4/2016 | Burke ................. A61M 5/1415 |
| | | | 604/179 |
| 2016/0193073 A1 | | 7/2016 | Kinsey |
| 2018/0256425 A1 | | 9/2018 | Lingenfelter |
| 2019/0101144 A1 | | 4/2019 | Scheffer |
| 2019/0344044 A1 * | | 11/2019 | Dickinson ........... A61M 25/002 |
| 2020/0001003 A1 * | | 1/2020 | Amir ......................... C09J 7/30 |

\* cited by examiner

DRAINAGE TUBING MANAGEMENT DEVICE

TECHNICAL FIELD

This application relates generally to medical devices and methods, and, more particularly, to urinary catheterization devices and methods.

BACKGROUND

Patients that are bedridden, incontinent, or undergoing surgery often require urinary catheters. Often, urinary catheters are provided in a closed-system format with the output of the catheter connected via drainage tubing to a collection bag or urine meter which is mounted to the side of the patient's bed. The drainage tubing is typically long and is sometimes longer than necessary to reach the collection bag or urine meter. This can cause dependent loops to form in the drainage tubing thereby causing urine to become trapped in the drainage tube, leading to a heighted risk of infection or urine blockage due to inadequate bladder pressure. Additionally, the drainage tubing can become tangled or can otherwise interfere with patient management.

It has now been found that a drainage tubing management device can be provided. The drainage tubing management device generally comprises a body or board, the body including protrusions that are spaced apart such that the drainage tubing can be secured between the protrusions. The protrusions are disposed in various positions along the body to allow the drainage tubing to be routed across the body. The device includes one or more posts or straps for securement to a hospital bed. The drainage tubing management device can thus be used to secure the drainage tubing and to accommodate unneeded length of the drainage tubing. In some cases, a kit that includes one or more posts and one or more straps may be provided, the kit allowing the clinician to choose whether posts or straps will be most suitable for securing the device to a particular hospital bed.

DETAILED DESCRIPTION

Figure 1:
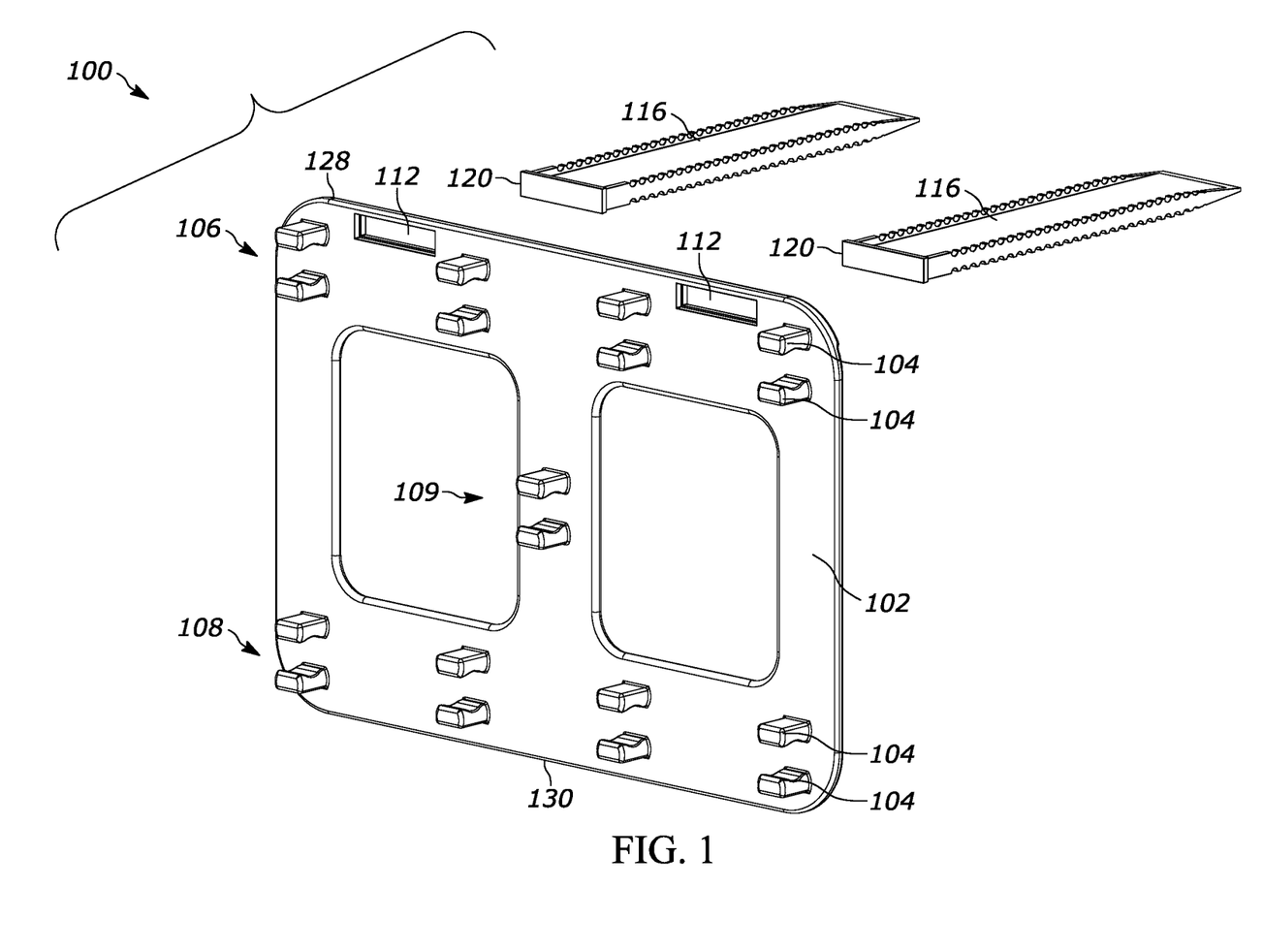
FIG. 1 is an exploded view of an exemplary drainage tubing management device.

The drainage tubing management device 100 shown in FIG. 1 generally includes a body 102 and posts 116. The body 102 includes apertures 112 into which the posts 116 are insertable. In some embodiments, the number of apertures 112 is equal to the number of posts 116, though such is not required.

The body 102 comprises a generally planar field. The body 102 includes plural pairs of protrusions 104 (not all pairs labeled in FIG. 1). The protrusions 104 extend from the body 102 in a direction generally normal to the body and are spaced apart such that a gap exists between the two protrusions 104 of the pair of protrusions. The pairs of protrusions 104 are sized and shaped to accept conventional urinary catheter drainage tubing, such that a length drainage tubing 110 can be secured between each pair of protrusions 104 via pressing the compressible tubing into the gaps between each pair of protrusions. The protrusions 104 can take any suitable shape (e.g., straight, concave, convex, etc.) as desired to retain the drainage tubing 110 in any pattern that is capable of avoiding dependent loops in the region of the body 102. As shown, the protrusions 104 take the form of opposing clips having radially outwardly curved surfaces.

Figure 3:
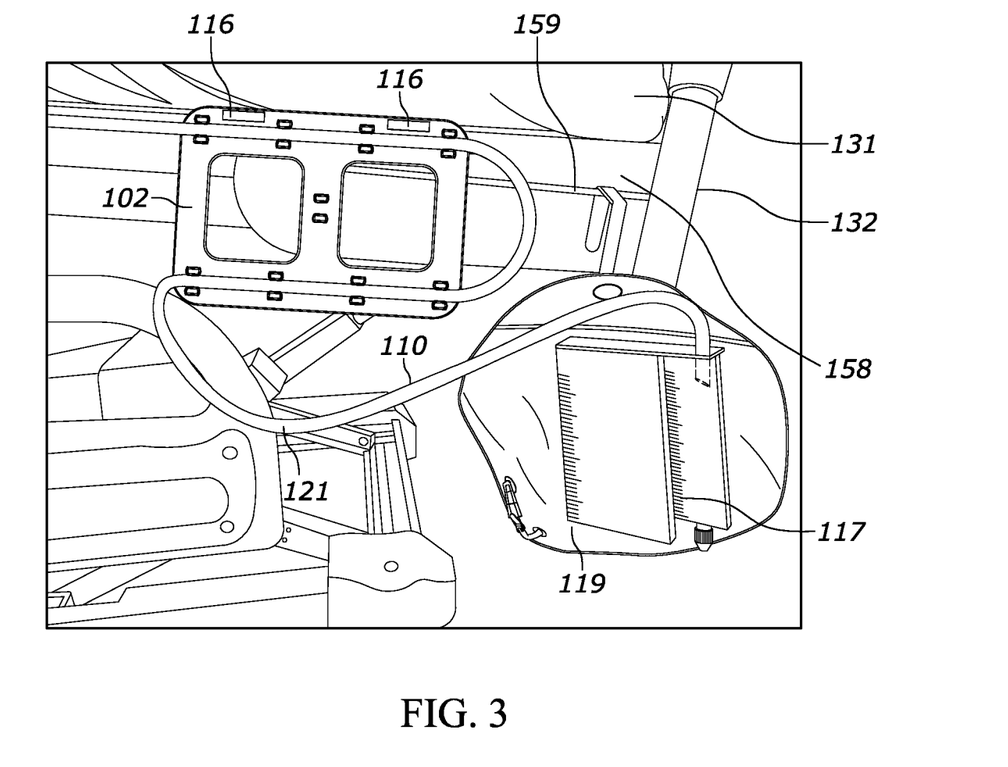
FIG. 3 is a front elevational view of a drainage tubing management device shown in FIGS. 1 and 2 and plural posts securing the body to a hospital bed, and illustrating retention of drainage tubing.
Figure 4:
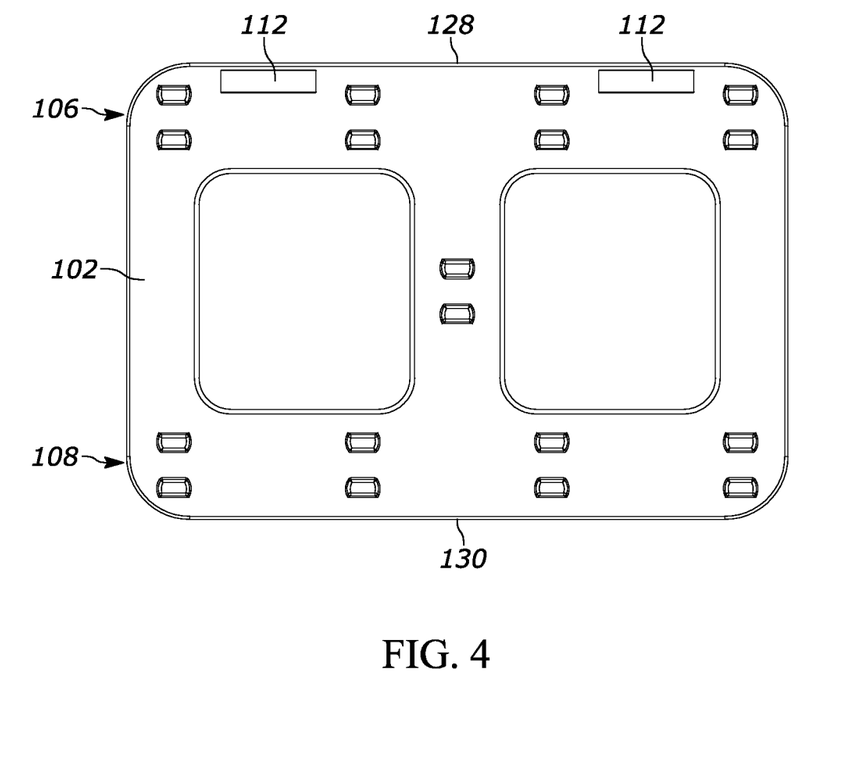
FIG. 4 is a front elevational view of the body of the drainage tubing management device shown in FIGS. 1 and 2.
Figure 5:
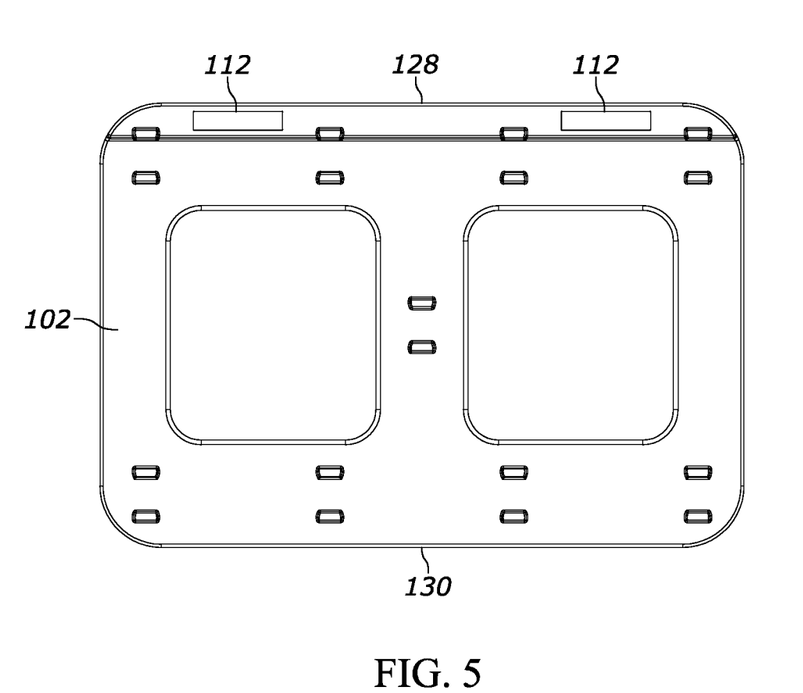
FIG. 5 is a rear elevational view of the body of the drainage tubing management device shown in FIG. 2.
Figure 11:
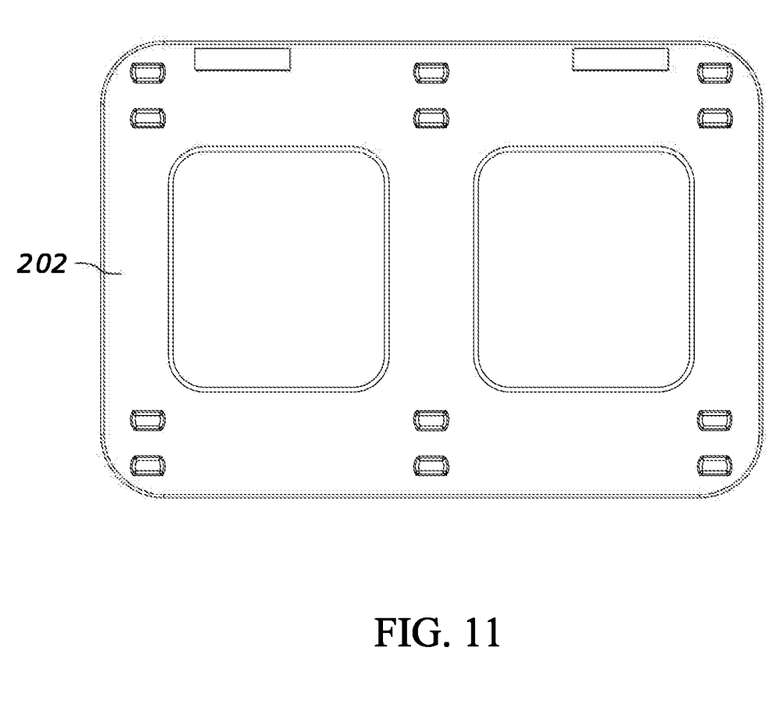
FIG. 11 is front elevational view of an alternative form of the body of a drainage tubing management device.

The pairs of protrusions 104 may be arranged in any pattern suitable to accept drainage tubing while avoiding dependent loops. At least some of the protrusions may be arranged in rows. In the embodiment depicted in FIG. 1, the body 102 includes two rows of four pairs of protrusions 104, which include a first row 106 and a second row 108. The body also includes a central pair of protrusions 109. The first row 106 of protrusions 104 is located proximal to a top edge 128 of the body 102 and the second row 108 of protrusions is located proximal to a bottom edge 130 of the body 102. Additionally, though the first row 106 and the second row 108 depicted in FIG. 3 are generally parallel to one another, such is not required. A larger or smaller number of protrusions may be provided in each row and a greater or smaller number of rows can be provided, and the protrusions may be arranged other than in rows. FIG. 11 for example depicts one alternative form for the body 202 including two rows each having three pairs of protrusions and no central protrusion.

Figure 2:
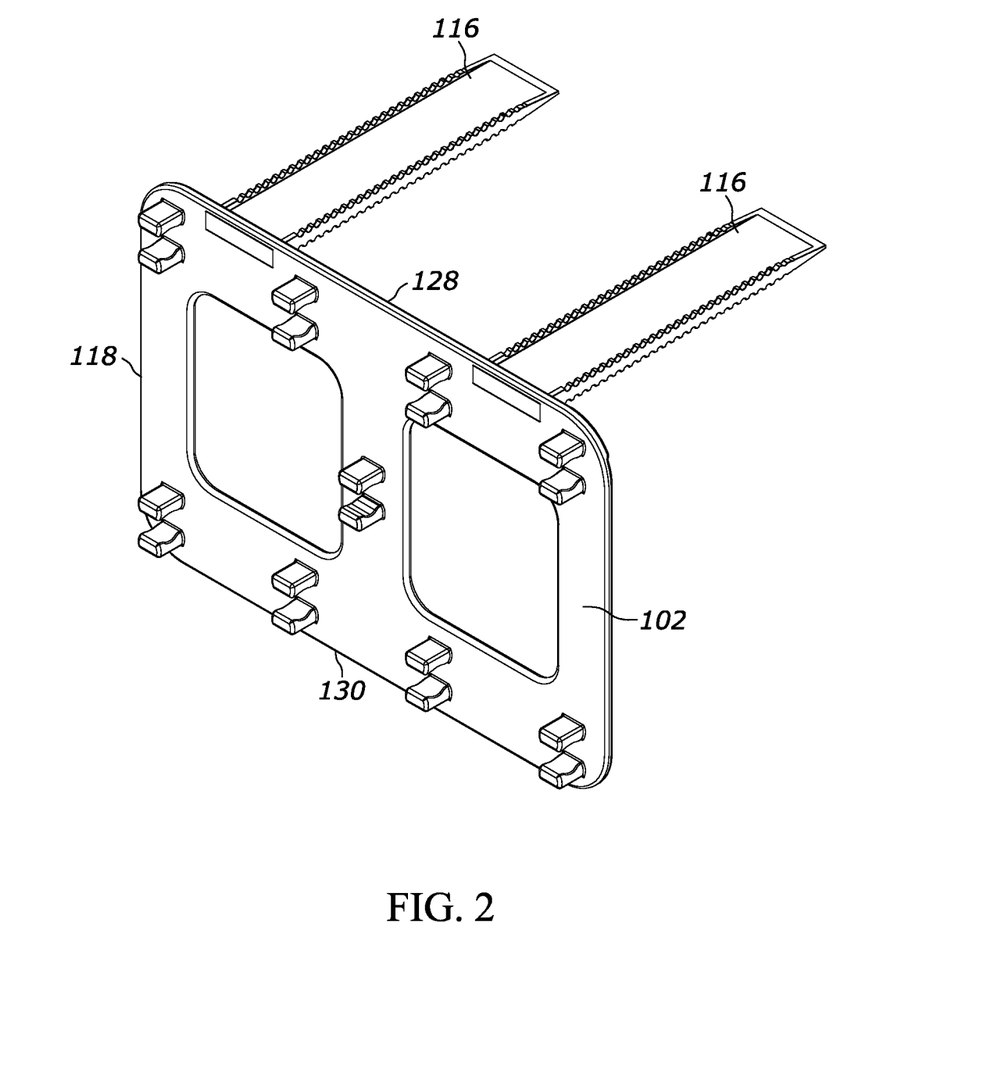
FIG. 2 is a perspective view of the drainage tubing management device shown in FIG. 1.

As seen in FIG. 2, the posts 116 have a terminal flange 120 and are insertable into and through the apertures 112, the flange 120 preventing passage of the post 116 completely through the aperture 112. The posts 116 are sufficiently rigid so as to support the body 102. As further depicted in FIG. 3, the posts 116 can be used to secure the board 102 to a bed 132 and hence can secure drainage tubing 110 without the formation of dependent loops. As shown, the posts 116 are inserted between the mattress 131 and bed frame 158 of the bed 132, but the posts 116 alternatively may be inserted between any surfaces as may be sufficient to support the body 102 and tubing 110. The drainage tubing 110 is secured to the protrusions 104 to accommodate excess length of the drainage tubing 110. The drainage tubing 110 can be routed in an "S" pattern across the body 102 by securing the drainage tubing 110 within the protrusions as illustrated or in any other suitable pattern. Though the drainage tubing 110 is depicted in FIG. 2 as passing through each of the pairs of protrusions 104 in rows 106 and 108, such is not required.

FIG. 3 further illustrates the drainage tubing terminating in a urine meter 117 that is hanging on a rod 159 disposed in front of rail 158. A drainage bag 119 is fluidically connected to the meter and is folded behind the meter in the position illustrated. The urine meter is optional and a drainage bag alone or another suitable drainage device may be employed. There is a depending bight 121 in the tubing 110 that may collect some urine in ordinary use, which is acceptable so long as no loops are formed in the tubing 110. If desired or if space permits, the meter 117 may be disposed a sufficient distance below the body 102 to allow tubing 110 to drop continuously between the body 102 and meter 117 such that urine can drain completely into the meter 117.

Figure 6:
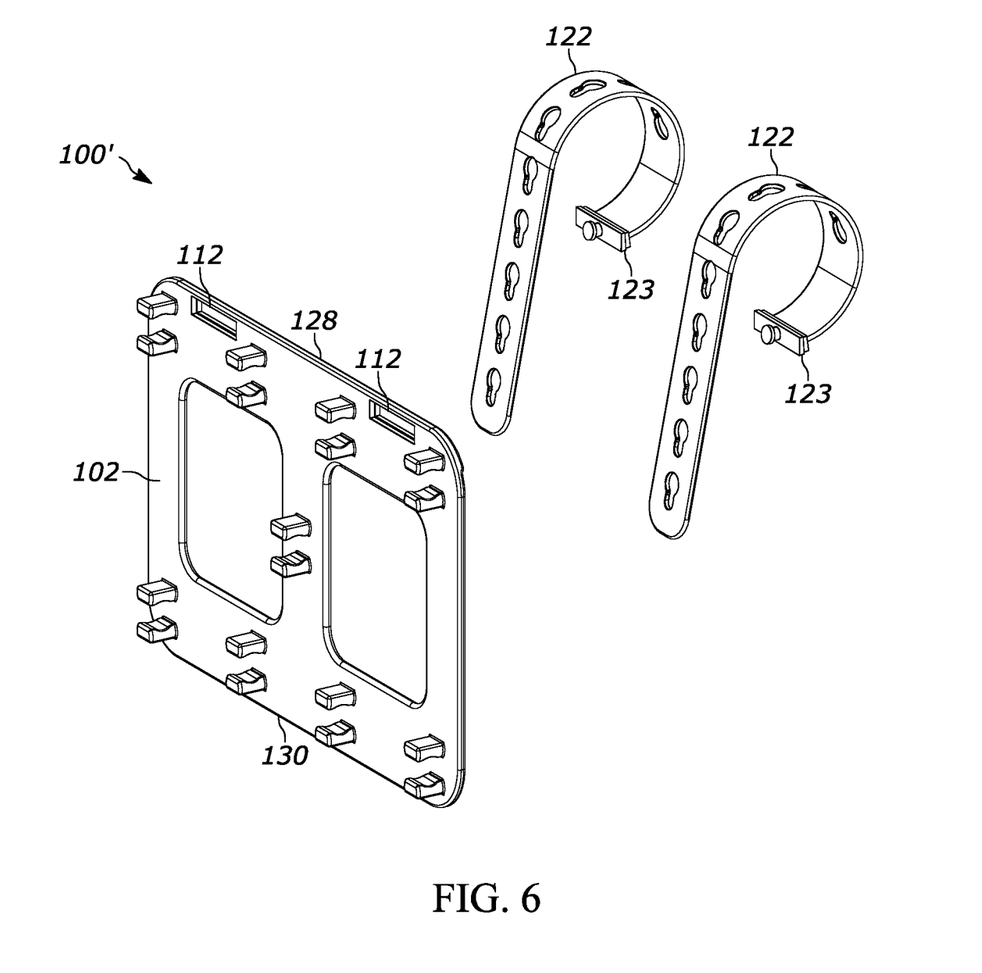
FIG. 6 is an exploded view of an alternative drainage tubing management device.
Figure 7:
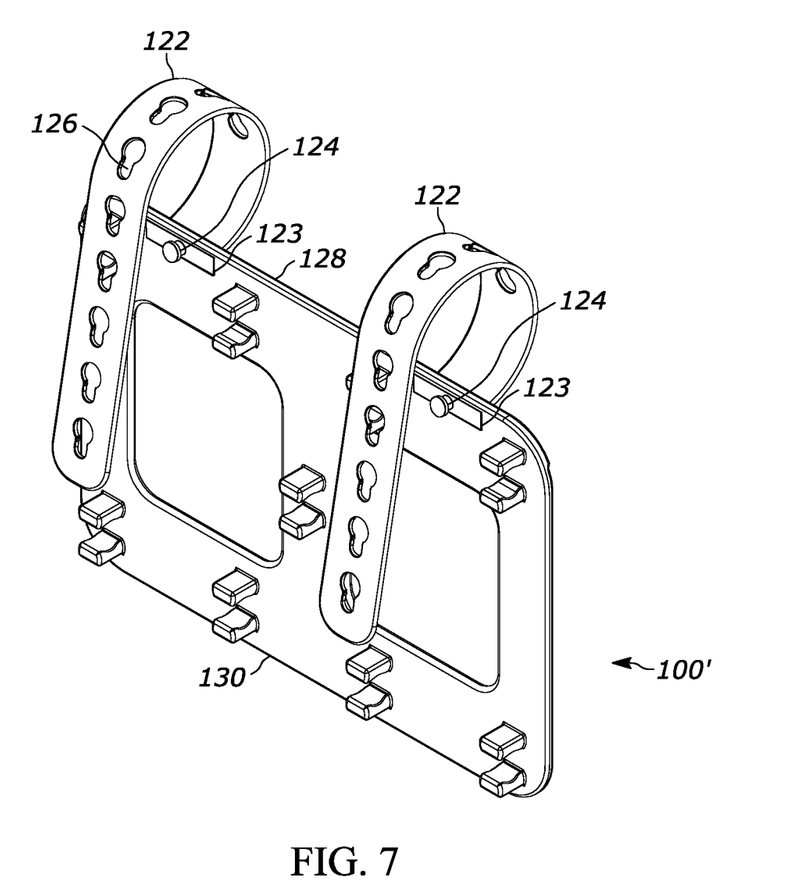
FIG. 7 is a perspective view of the drainage tubing management device shown in FIG. 6.
Figure 8:
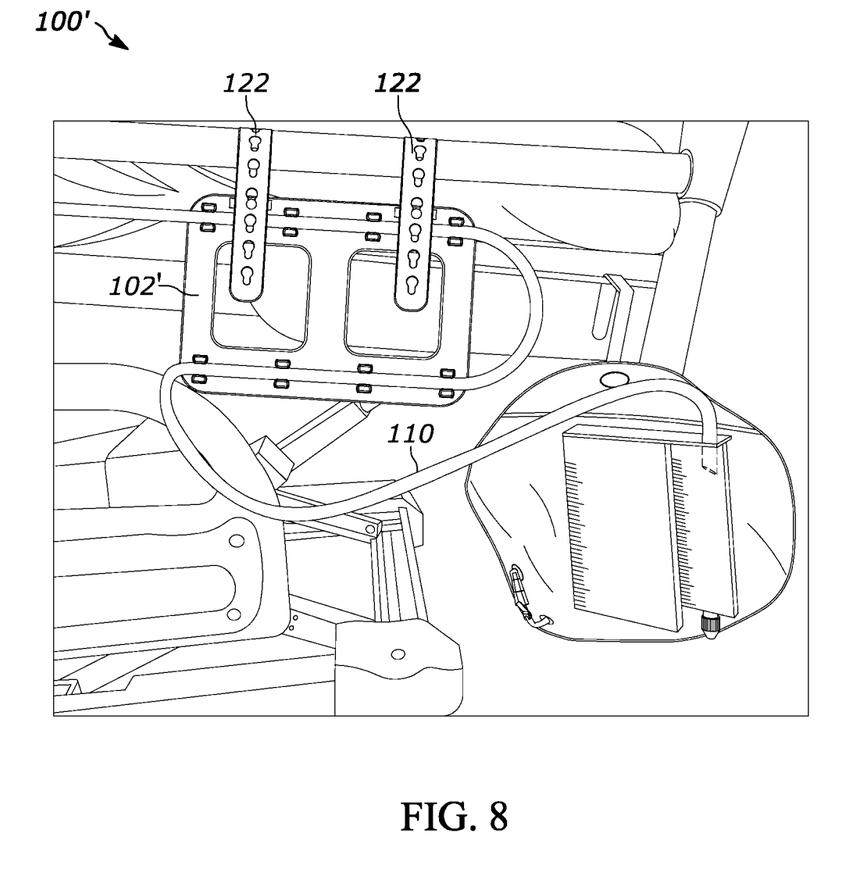
FIG. 8 is a front elevational view of a drainage tubing management device of FIG. 6 secured to the frame of a hospital bed, and illustrating retention of drainage tubing.

FIGS. 6-8 depict a drainage tubing management device 100' that includes a body 102' and that includes straps 122 and no posts. Body 102' is configured similarly to body 102 except that it omits the central pair of protrusions. Two straps are illustrated, but the device may have a greater or smaller number of straps. The straps 122 are insertable through the apertures 112. The straps 122 include flanges 123 that prevent the straps 122 from passing through the apertures 112. Each flange 123 includes a retaining post 124. The straps include a plurality of openings 126 that are engageable with the posts 124 to secure the strap 122 in a loop around a frame member. In one embodiment, the straps 122 can be looped about a bed frame 158 of a bed 132, as depicted in FIG. 8.

Figure 9:
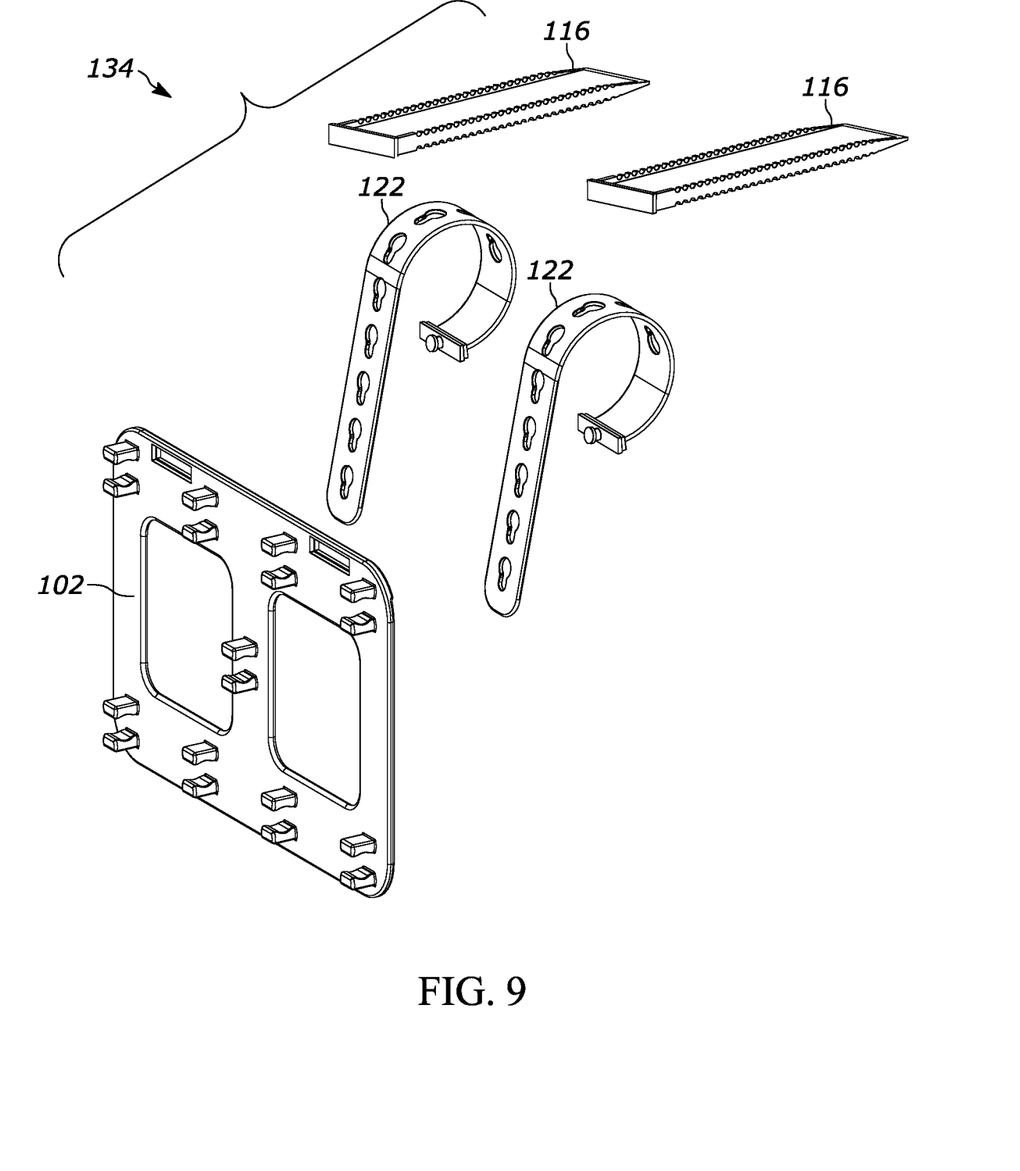
FIG. 9 illustrates a drainage tubing management kit having plural posts, plural straps, and a body.

A drainage tubing management kit 134 as shown in FIG. 9 includes the body 102, one or more straps 122, and one or more posts 116. Such a kit may allow the user to select between usage of straps 122 and/or posts 116 with the body 102, providing flexibility for different environments and mounting surfaces. The drainage tubing management kit 134 may include packaging (not shown) in which the body 102, straps 122, and posts 116 are stored.

Figure 10:
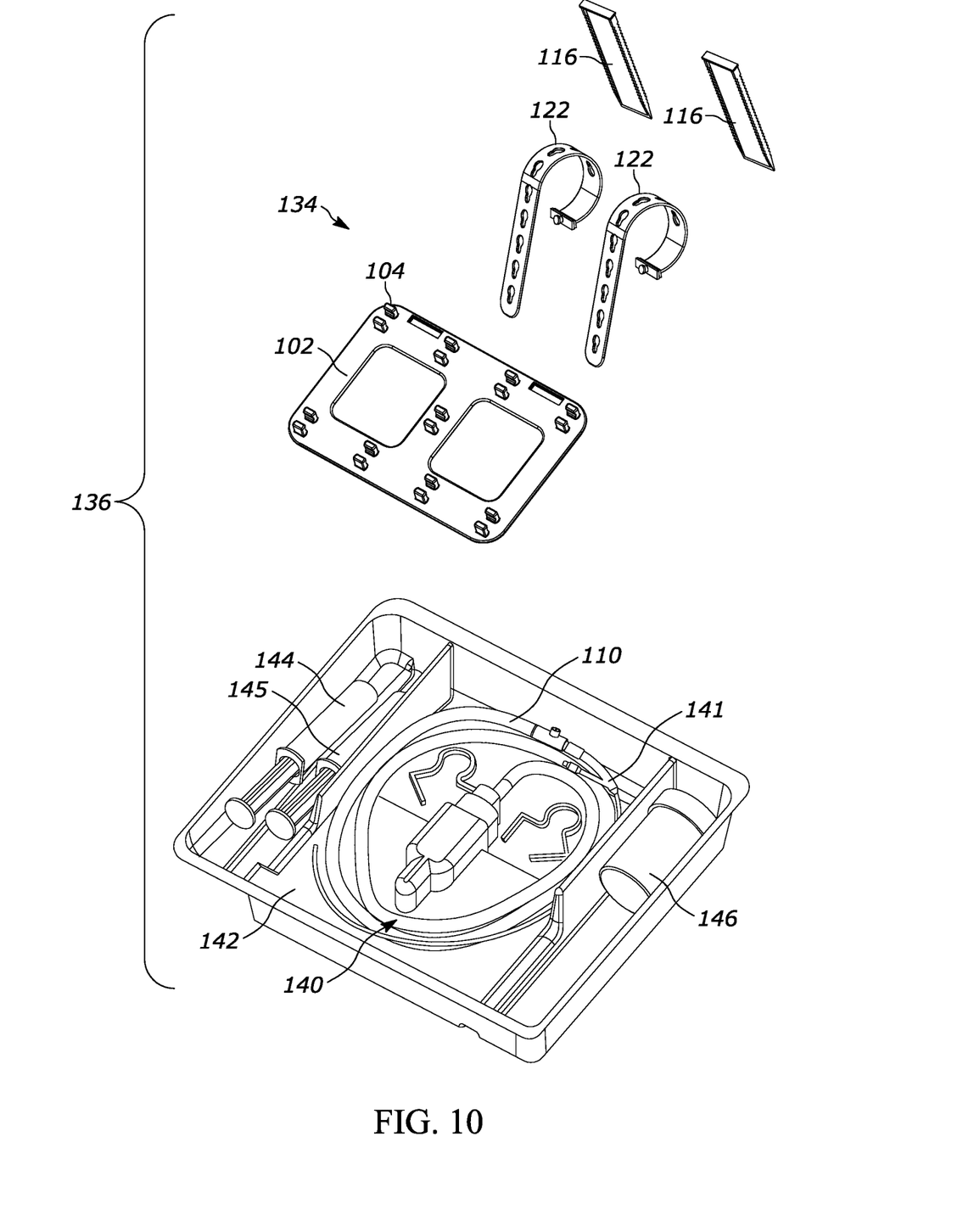
FIG. 10 is a representation of a catheterization kit including the drainage tubing management kit of FIG. 9.

Although the kit 134 may be supplied separately in its own packaging, in some embodiments the kit 134 can be provided as part of a larger catheterization kit 136, as depicted in FIG. 10. One such kit is described in more detail in U.S. Pat. No. 8,448,786, which is incorporated by reference in its entirety. Briefly, the kit includes a catheter assembly 140 that includes an indwelling catheter 141 connected by drainage tubing 110 to a drainage bag 142. A urine meter as depicted in FIGS. 3 and 8 optionally may be included. The kit includes a first, upper syringe 144 for inflation of the balloon of the indwelling catheter, and a second syringe 145 containing lubricant. The first and second syringes being disposed in a compartment of the tray that is adjacent the compartment housing the catheter assembly. The kit includes cleaning implements, an outer wrap, and an underpad (not shown) and is disposed within outer packaging (also not shown) and a specimen jar 146. The kit 134 may be disposed at any location within the outer packaging of the kit, and may be provided in its own package within the outer packaging.

The body and the posts can be made of any material sufficiently rigid to allow the body and posts to function the purposes described herein, such as metal, a suitable plastic, or rubber. When the device is contemplated to be a disposable device for single use, the body and the posts may be made of polypropylene. The straps are flexible and can be made of any material suitable to support the body and tubing, such as a suitable plastic, rubber, or cloth. For a disposable single-use device, the straps may be made of low-density polyethylene (LDPE). All parts may be manufactured using conventional polymer forming techniques.

It is thus seen that the present disclosure provides a drainage tubing management device that is useful in securing drainage tubing while preventing or inhibiting the formation of dependent loops.

All methods described herein can be performed in any suitable order unless otherwise indicated herein or otherwise clearly contradicted by context. The use of any and all examples, or language describing an example (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A drainage tubing management kit comprising:
   a drainage tubing management device, the drainage tubing management device comprising:
   a body including a generally planar field, and having plural spaced apart protrusions extending from the field, each pair of protrusions sized to accept flexible drainage tubing therebetween, wherein the pairs of protrusions are arranged in at least first and second rows such that the flexible drainage tubing may be retained with respect to the body along the at least first and second rows;
   at least one aperture in the body; and
   a post having a longitudinal axis, the post having a first end portion being insertable through the at least one aperture and an opposite second end portion having a terminal flange occluding passage of the post through the at least one aperture, the post being sufficiently rigid to support the body; and
   a flexible hanging strap having a first end portion sized for insertion through the at least one aperture and an opposite second end portion having a terminal flange occluding passage of the strap through the at least one aperture.

2. The drainage tubing management kit of claim 1, wherein the at least first and second rows are generally parallel to one another.

3. The drainage tubing management kit of claim 1, wherein the body has a top edge and a bottom edge, and wherein the first row of the pairs of protrusions is located proximal to the top edge and the second row of the pairs of protrusions is located in proximity to the bottom edge.

4. The drainage tubing management kit of claim 1, wherein the body further includes at least one additional pair of protrusions disposed between the at least first and second rows.

5. The drainage tubing management kit of claim 1, wherein the body includes at least two apertures, the kit including at least two posts each having a longitudinal axis, each of the at least two posts being insertable through one of the at least two apertures and having a terminal flange occluding passage of one of the at least two posts through one of the at least two apertures.

6. The drainage tubing management kit of claim 1, wherein the body includes at least two apertures, the kit including at least two flexible hanging straps each insertable one of the at least two apertures and having a terminal flange occluding passage of one of the at least two flexible handing straps through one of the at least two apertures.

7. The drainage tubing management kit of claim 1, wherein the body includes at least two apertures, the kit including at least two posts having a longitudinal axis, each of the at least two posts being insertable through one of the at least two apertures and having a terminal flange occluding passage of one of the at least two posts through one of the at least two apertures, the kit further including at least two flexible hanging straps each insertable through one of the at least two apertures and having a terminal flange occluding passage of one of the at least two flexible hanging straps through one of the at least two apertures.

8. The drainage tubing management kit of claim 1, wherein the terminal flange of the flexible hanging strap has a retaining post and the flexible hanging strap includes plural openings engageable with the retaining post.

9. A catheterization kit, comprising
   a tray holding a urinary catheter connected via the flexible drainage tubing to a drainage bag, and
   the drainage tubing management kit of claim 1.

* * * * *

UNITED STATES PATENT AND TRADEMARK OFFICE
CERTIFICATE OF CORRECTION

| | | |
|---|---|---|
| PATENT NO. | : 11,420,024 B2 | Page 1 of 1 |
| APPLICATION NO. | : 16/775495 | |
| DATED | : August 23, 2022 | |
| INVENTOR(S) | : Connor Feeney and Andrew J. Mills | |

It is certified that error appears in the above-identified patent and that said Letters Patent is hereby corrected as shown below:

In the Claims

Claim 6, Column 5, Line 7, delete "handing" and insert --hanging--.

Signed and Sealed this
Eighth Day of November, 2022

Katherine Kelly Vidal
*Director of the United States Patent and Trademark Office*